(12) United States Patent
Bezzek

(10) Patent No.: US 8,846,061 B1
(45) Date of Patent: Sep. 30, 2014

(54) MULTIVITAMIN-MINERAL REGIMENS FOR LONGEVITY AND WELLNESS

(71) Applicant: Mark S. Bezzek, Chapel Hill, NC (US)

(72) Inventor: Mark S. Bezzek, Chapel Hill, NC (US)

( * ) Notice: Subject to any disclaimer, the term of this patent is extended or adjusted under 35 U.S.C. 154(b) by 91 days.

(21) Appl. No.: 13/693,563

(22) Filed: Dec. 4, 2012

Related U.S. Application Data

(63) Continuation-in-part of application No. 13/043,056, filed on Mar. 8, 2011, now Pat. No. 8,343,517, and a continuation-in-part of application No. 13/043,216, filed on Mar. 8, 2011, now Pat. No. 8,349,376.

(51) Int. Cl.

| | | |
|---|---|---|
| A61K 9/00 | (2006.01) | |
| A61K 36/88 | (2006.01) | |
| A61K 36/48 | (2006.01) | |
| A61K 36/45 | (2006.01) | |
| A61K 36/03 | (2006.01) | |
| A61K 31/122 | (2006.01) | |
| A61K 36/68 | (2006.01) | |
| A61K 36/484 | (2006.01) | |
| A61K 36/42 | (2006.01) | |
| A61K 36/54 | (2006.01) | |
| A61K 36/27 | (2006.01) | |
| A61K 36/82 | (2006.01) | |
| A61K 36/258 | (2006.01) | |

(52) U.S. Cl.
CPC ............... *A61K 36/88* (2013.01); *A61K 36/48* (2013.01); *A61K 36/45* (2013.01); *A61K 36/03* (2013.01); *A61K 31/122* (2013.01); *A61K 36/68* (2013.01); *A61K 36/484* (2013.01); *A61K 36/42* (2013.01); *A61K 36/54* (2013.01); *A61K 36/27* (2013.01); *A61K 36/82* (2013.01); *A61K 36/258* (2013.01)
USPC ......................................................... 424/400

(58) Field of Classification Search
None
See application file for complete search history.

(56) References Cited

U.S. PATENT DOCUMENTS

| | | | |
|---|---|---|---|
| 4,752,479 A | 6/1988 | Briggs et al. | |
| 4,897,388 A | 1/1990 | Malluche | |
| 5,484,593 A * | 1/1996 | Iwasaki et al. | ................ 424/774 |
| 5,494,678 A | 2/1996 | Paradissis et al. | |
| 5,798,392 A | 8/1998 | Moss | |
| 5,885,608 A | 3/1999 | McEntee | |
| 5,962,535 A | 10/1999 | Miyamoto et al. | |
| 5,994,322 A | 11/1999 | Masuda et al. | |
| 6,326,031 B1 * | 12/2001 | Hsia et al. | ...................... 424/523 |
| 6,352,712 B1 * | 3/2002 | Lukaczer et al. | ............. 424/439 |
| 6,372,760 B1 | 4/2002 | Kato et al. | |

(Continued)

FOREIGN PATENT DOCUMENTS

WO  2009009393 A2  1/2009

OTHER PUBLICATIONS

Bottiglieri et al.; Cerebrospinal fluid S-adenosylmethionine in depression and dementia: effects of treatment with parenteral and oral S-adenosylmethionine; Journal of Neurology, Neurosurgery, and Psychiatry; 53, pp. 1096-1098; published 1990.

(Continued)

*Primary Examiner* — Brian Gulledge

(57) ABSTRACT

Dietary vitamin-mineral supplements featuring various vitamins and minerals for benefiting individuals suffering from conditions such as nutritional deficiencies, vitamin deficiencies, aging, cancer, high blood pressure, high cholesterol, dementia, Alzheimer's disease, coronary artery disease, fatigue, and stroke. Vitamins and minerals may include Vitamin C, Vitamin A, pregnenolone, coenzyme Q10, Vitamin K2, acetyl L-carnitine arginate, L-glutathione, among others.

20 Claims, 24 Drawing Sheets

LONGEVITY FORMULATION (45 COMPONENTS)

| | |
|---|---|
| pregnenolone at about 30 mg; | turmeric extract at about 8 gms; |
| natto kinase at about 300 mg; | green tea extract; |
| coenzyme Q10 at about 300 mg; | gingko leaf extract at about 140 mg; |
| acetyl L-carnitine arginate at about 700 mg; | bilberry extracts at about 600 mg; |
| L-glutathione at about 250 mg; | rutin at about 100 mg; |
| vitamin A; | blain pepper fruit extract at about 3 mg; |
| vitamin C at about 2000 mg; | lycopene at about 110 mg; |
| vitamin D3 at about 8000 IU; | lutein at about 20 mg; |
| vitamin E at about 1000 mg; | astaxanthin at about 20 mg; |
| niacinamide at about 1000 mg; | bitter melon at about 1000 mg; |
| calcium at about 1000 mg; | dehydroeplandrosterone at about 2000 mg; |
| chromium at about 1200 mcg; | black currant seed at about 2000 mg; |
| aged garlic at about 1000 mg; | carnosine at about 3 gms; |
| N-acetyl cysteine at about 600 mg; | conjugated linoleic acid at about 3000 mg; |
| vanadyl sulphate at about 400 mg; | hyaluronic acid at about 80 mg. |
| silymarin at about 600 mg; | |
| D-ribose at about 10 gms | |
| indole 3 carbinol at about 200 mg; | |
| sulphoramane at about 225 mg; | |
| cranberry vaccinium macrocarpon at about 1000 mg; | |
| French maritime pine bark extract at about 250 mg; | |
| cinnamomum roct at about 4000 mg; | |
| inositol at about 1000 mg; | |
| alpha-lipoic acid and r lipoic acid at about 600 mg; | |
| polygonum cuspidatum root extract at about 1000 mg | |
| dimethylaminoethanol at about 30 mg; | |
| grape seed extract at about 300 mg; | |
| methylsulfonylmethane at about 250 mg; | |
| hawthorn berry extract at about 1500 mg; | |
| N-acetyl tyrosine at about 25 mg; | |

(56) References Cited

U.S. PATENT DOCUMENTS

| | | |
|---|---|---|
| 6,500,798 B1 | 12/2002 | Stanton et al. |
| 6,733,797 B1 | 5/2004 | Summers |
| 6,953,588 B2 | 10/2005 | Cooper et al. |
| 6,953,794 B2 | 10/2005 | Wischik et al. |
| 6,964,969 B2 | 11/2005 | McCleary |
| D553,734 S | 10/2007 | Chen et al. |
| 7,935,365 B2 | 5/2011 | Dror et al. |
| 2001/0036949 A1 | 11/2001 | Coe et al. |
| 2002/0155163 A1 | 10/2002 | Benjamin et al. |
| 2003/0171385 A1 | 9/2003 | Alkon et al. |
| 2005/0123669 A1 | 6/2005 | Yamada |
| 2005/0214383 A1 | 9/2005 | Bubnis et al. |
| 2005/0234248 A1 | 10/2005 | Kossler et al. |
| 2006/0057231 A1* | 3/2006 | Rimando et al. ............... 424/732 |
| 2006/0088610 A1 | 4/2006 | Vorsa et al. |
| 2006/0122270 A1 | 6/2006 | Henderson |
| 2006/0127505 A1 | 6/2006 | Haines et al. |
| 2006/0211721 A1 | 9/2006 | Roberts |
| 2006/0257502 A1 | 11/2006 | Liu |
| 2007/0060644 A1 | 3/2007 | Vander Jagt et al. |
| 2007/0116779 A1 | 5/2007 | Mazzio |
| 2007/0128272 A1 | 6/2007 | Zerbe et al. |
| 2008/0213401 A1 | 9/2008 | Smith |
| 2008/0214649 A1 | 9/2008 | Yu et al. |
| 2009/0074677 A1 | 3/2009 | Marx et al. |
| 2010/0021533 A1 | 1/2010 | Mazed et al. |

OTHER PUBLICATIONS

Imagawa et al.; Coenzyme Q10, iron, and vitamin B6 in genetically-confirmed Alzheimer's disease; The Lancet; vol. 340; issue 8820; p. 671; published Sep. 12, 1992.

* cited by examiner

LONGEVITY FORMULATION (45 COMPONENTS)

| | |
|---|---|
| pregnenolone at about 30 mg; | turmeric extract at about 8 gms; |
| natto kinase at about 300 mg; | green tea extract; |
| coenzyme Q10 at about 300 mg; | gingko leaf extract at about 140 mg; |
| acetyl L-carnitine arginate at about 700 mg; | bilberry extracts at about 600 mg; |
| L-glutathione at about 250 mg; | rutin at about 100 mg; |
| vitamin A; | blain pepper fruit extract at about 3 mg; |
| vitamin C at about 2000 mg; | lycopene at about 110 mg; |
| vitamin D3 at about 8000 IU; | lutein at about 20 mg; |
| vitamin E at about 1000 mg; | astaxanthin at about 20 mg; |
| niacinamide at about 1000 mg; | bitter melon at about 1000 mg; |
| calcium at about 1000 mg; | dehydroepiandrosterone at about 2000 mg; |
| chromium at about 1200 mcg; | black currant seed at about 2000 mg; |
| aged garlic at about 1000 mg; | carnosine at about 3 gms; |
| N-acetyl cysteine at about 600 mg; | conjugated linoleic acid at about 3000 mg; |
| vanadyl sulphate at about 400 mg; | hyaluronic acid at about 80 mg. |
| silymarin at about 600 mg; | |
| D-ribose at about 10 gms | |
| indole 3 carbinol at about 200 mg; | |
| sulphoramane at about 225 mg; | |
| cranberry vaccinium macrocarpon at about 1000 mg; | |
| French maritime pine bark extract at about 250 mg; | |
| cinnamomum root at about 4000 mg; | |
| inositol at about 1000 mg; | |
| alpha-lipoic acid and r lipoic acid at about 600 mg; | |
| polygonum cuspidatum root extract at about 1000 mg | |
| dimethylaminoethanol at about 30 mg; | |
| grape seed extract at about 300 mg; | |
| methylsulfonylmethane at about 250 mg; | |
| hawthorn berry extract at about 1500 mg; | |
| N-acetyl tyrosine at about 25 mg; | |

FIG. 1

LONGEVITY FORMULATION (40 COMPONENTS)

| | |
|---|---|
| pregnenolone at about 30 mg; | rutin at about 100 mg; |
| natto kinase at about 300 mg; | lycopene at about 110 mg; |
| coenzyme Q10 at about 300 mg; | lutein at about 20 mg; |
| acetyl L-carnitine arginate at about 700 mg; | astaxanthin at about 20 mg; |
| L-glutathione at about 250 mg; | bitter melon at about 1000 mg; |
| vitamin D3 at about 8000 IU; | dehydroepiandrosterone at about 2000 mg; |
| vitamin E at about 1000 mg; | black currant seed at about 2000 mg; |
| niacinamide at about 1000 mg; | carnosine at about 3 gms; |
| chromium at about 1200 mcg; | conjugated linoleic acid at about 3000 mg; |
| aged garlic at about 1000 mg; | hyaluronic acid at about 80 mg. |
| N-acetyl cysteine at about 600 mg; | |
| vanadyl sulphate at about 400 mg; | |
| silymarin at about 600 mg; | |
| D-ribose at about 10 gms | |
| indole 3 carbinol at about 200 mg; | |
| sulphoramane at about 225 mg; | |
| cranberry vaccinium macrocarpon at about 1000 mg; | |
| French maritime pine bark extract at about 250 mg; | |
| cinnamomum root at about 4000 mg; | |
| inositol at about 1000 mg; | |
| alpha-lipoic acid and r lipoic acid at about 600 mg; | |
| dimethylaminoethanol at about 30 mg; | |
| grape seed extract at about 300 mg; | |
| methylsulfonylmethane at about 250 mg; | |
| hawthorn berry extract at about 1500 mg; | |
| N-acetyl tyrosine at about 25 mg; | |
| turmeric extract at about 8 gms; | |
| green tea extract; | |
| gingko leaf extract at about 140 mg; | |
| bilberry extracts at about 600 mg; | |

FIG. 2

LONGEVITY FORMULATION (35 COMPONENTS)

| | |
|---|---|
| pregnenolone at about 30 mg; | bitter melon at about 1000 mg; |
| natto kinase at about 300 mg; | dehydroepiandrosterone at about 2000 mg; |
| coenzyme Q10 at about 300 mg; | carnosine at about 3 gms; |
| acetyl L-carnitine arginate at about 700 mg; | conjugated linoleic acid at about 3000 mg; |
| L-glutathione at about 250 mg; | hyaluronic acid at about 80 mg. |
| niacinamide at about 1000 mg; | |
| chromium at about 1200 mcg; | |
| aged garlic at about 1000 mg; | |
| N-acetyl cysteine at about 600 mg; | |
| vanadyl sulphate at about 400 mg; | |
| silymarin at about 600 mg; | |
| D-ribose at about 10 gms | |
| indole 3 carbinol at about 200 mg; | |
| sulphoramane at about 225 mg; | |
| cranberry vaccinium macrocarpon at about 1000 mg; | |
| cinnamomum root at about 4000 mg; | |
| inositol at about 1000 mg; | |
| alpha-lipoic acid and r lipoic acid at about 600 mg; | |
| dimethylaminoethanol at about 30 mg; | |
| grape seed extract at about 300 mg; | |
| methylsulfonylmethane at about 250 mg; | |
| hawthorn berry extract at about 1500 mg; | |
| turmeric extract at about 8 gms; | |
| green tea extract; | |
| gingko leaf extract at about 140 mg; | |
| bilberry extracts at about 600 mg; | |
| rutin at about 100 mg; | |
| lycopene at about 110 mg; | |
| lutein at about 20 mg; | |
| astaxanthin at about 20 mg; | |

FIG. 3

LONGEVITY FORMULATION (30 COMPONENTS)

| |
|---|
| pregnenolone at about 30 mg; |
| natto kinase at about 300 mg; |
| coenzyme Q10 at about 300 mg; |
| acetyl L-carnitine arginate at about 700 mg; |
| L-glutathione at about 250 mg; |
| aged garlic at about 1000 mg; |
| N-acetyl cysteine at about 600 mg; |
| vanadyl sulphate at about 400 mg; |
| silymarin at about 600 mg; |
| D-ribose at about 10 gms |
| indole 3 carbinol at about 200 mg; |
| sulphoramane at about 225 mg; |
| cranberry vaccinium macrocarpon at about 1000 mg; |
| cinnamomum root at about 4000 mg; |
| inositol at about 1000 mg; |
| alpha-lipoic acid and r lipoic acid at about 600 mg; |
| dimethylaminoethanol at about 30 mg; |
| grape seed extract at about 300 mg; |
| methylsulfonylmethane at about 250 mg; |
| hawthorn berry extract at about 1500 mg; |
| turmeric extract at about 8 gms; |
| green tea extract; |
| gingko leaf extract at about 140 mg; |
| bilberry extracts at about 600 mg; |
| rutin at about 100 mg; |
| lycopene at about 110 mg; |
| lutein at about 20 mg; |
| astaxanthin at about 20 mg; |
| dehydroepiandrosterone at about 2000 mg; |
| carnosine at about 3 gms; |

FIG. 4

ANTI-DEMENTIA FORMULATION (35 COMPONENTS)

| | |
|---|---|
| idebenone at about 180 mg; | dimethylethanolamine at about 100 mg; |
| rhodiola at about 400 mg; | s-adenosylmethionine at about 400 mg; |
| gingko biloba at about 160 mg; | colostrum at about 4000 mg; |
| huperzine a at about 2 mg; | lecithin at about 300 mg; |
| coenzyme Q10 at about 400 mg; | vitamin D2 at about 8000 IU |
| alpha lipoic acid at about 600 mg; | |
| melatonin at about 3 mg; | |
| omega 3 fatty acid at about 6000 mg; | |
| zinc carnosine at about 500 mg; | |
| magnesium at about 1000mg; | |
| n-acetyl cysteine at about 1200 mg; | |
| dehydroepiandrosterone at about 100 mg; | |
| pregnenolone at about 60 mg; | |
| phosphotidylserine docasahexanenoic acid; | |
| vinpocetine at about 40 mg; | |
| grapeseed extract at about 300 mg; | |
| blueberry extract at about 300 mg; | |
| acetyl l-carnitine arginate 900 mg; | |
| ashwagandha extract at about 250 mg; | |
| uridine 5 monophosphate at about 100 mg; | |
| French maritime pine bark extract at about 250 mg; | |
| l-alpha-glycerylphosphorylcholine at about 1500 mg; | |
| curcumin at about 8 gms; | |
| coconut oil at about 1000 mg; | |
| astaxanthin at about 20 mg; | |
| chromium picolinate at about 1200 mg; | |
| carnosine at about 3000mg; | |
| n-acetyl-tyrosine at about 1500mg; | |
| phenylalanine at about 1500 mg; | |
| quercetin at about 150 mg; | |

FIG. 5

ANTI-DEMENTIA FORMULATION (30 COMPONENTS)

| |
|---|
| idebenone at about 180 mg; |
| rhodiola at about 400 mg; |
| gingko biloba at about 160 mg; |
| huperzine a at about 2 mg; |
| coenzyme Q10 at about 400 mg; |
| alpha lipoic acid at about 600 mg; |
| melatonin at about 3 mg; |
| omega 3 fatty acid at about 6000 mg; |
| zinc carnosine at about 500 mg; |
| n-acetyl cysteine at about 1200 mg; |
| dehydroepiandrosterone at about 100 mg; |
| pregnenolone at about 60 mg; |
| phosphotidylserine docasahexanenoic acid; |
| vinpocetine at about 40 mg; |
| grapeseed extract at about 300 mg; |
| blueberry extract at about 300 mg; |
| acetyl l-carnitine arginate 900 mg; |
| ashwagandha extract at about 250 mg; |
| uridine 5 monophosphate at about 100 mg; |
| French maritime pine bark extract at about 250 mg; |
| l-alpha-glycerylphosphorylcholine at about 1500 mg; |
| curcumin at about 8 gms; |
| coconut oil at about 1000 mg; |
| astaxanthin at about 20 mg; |
| chromium picolinate at about 1200 mg; |
| carnosine at about 3000mg; |
| n-acetyl-tyrosine at about 1500mg; |
| quercetin at about 150 mg; |
| s-adenosylmethionine at about 400 mg; |
| lecithin at about 300 mg; |

FIG. 6

ANTI-DEMENTIA FORMULATION (25 COMPONENTS)

| |
|---|
| idebenone at about 180 mg; |
| huperzine a at about 2 mg; |
| alpha lipoic acid at about 600 mg; |
| melatonin at about 3 mg; |
| omega 3 fatty acid at about 6000 mg; |
| zinc carnosine at about 500 mg; |
| n-acetyl cysteine at about 1200 mg; |
| dehydroepiandrosterone at about 100 mg; |
| pregnenolone at about 60 mg; |
| phosphotidylserine docasahexanenoic acid; |
| vinpocetine at about 40 mg; |
| grapeseed extract at about 300 mg; |
| blueberry extract at about 300 mg; |
| acetyl l-carnitine arginate 900 mg; |
| ashwagandha extract at about 250 mg; |
| uridine 5 monophosphate at about 100 mg; |
| l-alpha-glycerylphosphorylcholine at about 1500 mg; |
| curcumin at about 8 gms; |
| coconut oil at about 1000 mg; |
| astaxanthin at about 20 mg; |
| carnosine at about 3000mg; |
| n-acetyl-tyrosine at about 1500mg; |
| quercetin at about 150 mg; |
| s-adenosylmethionine at about 400 mg; |
| lecithin at about 300 mg; |

FIG. 7

DIABETIC TREATMENT FORMULATION (35 COMPONENTS)

| | |
|---|---|
| bilberry extract at about 600 mg; | Banaba leaf at about 50 mg; |
| alpha lipoic acid at about 600 mg; | Bromocriptine at about 2.5 mg; |
| chromium picolinate at about 1200 mcg; | Benfotiamine at about 400 mg; |
| omega-3-fatty acids at about 8 g; | Resveratrol at about 250 mg; |
| dihydroepiandrosterone at about 100 mg; | Pterostilbene at about 1 mg |
| Blueberry extract at about 500 mg; | |
| Vitamin D3 at about 5000 IU; | |
| Psyllium at about 5 g; | |
| Guar gum at about 500 mg; | |
| Carnosine at about 3,000 mg; | |
| Cinnamomum root at about 2 g; | |
| Aged garlic at about 1,000 mg; | |
| Vanadium at about 50 mg; | |
| Bitter melon at about 1,000 mg; | |
| Green tea extract at about 450 mg; | |
| Zinc citrate at about 50 mg; | |
| Fenugreek 1:4 at about 80 mg; | |
| Goat's rue; | |
| Curcumin at about 8 g; | |
| Glycyrrhiza glabra at about 500 mg; | |
| Vitamin E at about 1,000 mg; | |
| Coenzyme Q10 at about 300 mg; | |
| Vitamin C at about 3,000 mg; | |
| Gymnema at about 400 mg; | |
| L-arginine at about 10 g; | |
| Ginseng; | |
| L-carnitine at about 4 g; | |
| Pyrroloquinoline quinone at about 20 mg; | |
| Brown seaweed extract; | |
| Bladderwrack; | |

FIG. 8

DIABETIC TREATMENT FORMULATION (30 COMPONENTS)

| |
|---|
| bilberry extract at about 600 mg; |
| alpha lipoic acid at about 600 mg; |
| chromium picolinate at about 1200 mcg; |
| omega-3-fatty acids at about 8 g; |
| dihydroepiandrosterone at about 100 mg; |
| Blueberry extract at about 500 mg; |
| Vitamin D3 at about 5000 IU; |
| Psyllium at about 5 g; |
| Guar gum at about 500 mg; |
| Carnosine at about 3,000 mg; |
| Cinnamomum root at about 2 g; |
| Aged garlic at about 1,000 mg; |
| Vanadium at about 50 mg; |
| Bitter melon at about 1,000 mg; |
| Green tea extract at about 450 mg; |
| Zinc citrate at about 50 mg; |
| Fenugreek 1:4 at about 80 mg; |
| Goat's rue; |
| Curcumin at about 8 g; |
| Glycyrrhiza glabra at about 500 mg; |
| Vitamin E at about 1,000 mg; |
| Coenzyme Q10 at about 300 mg; |
| Vitamin C at about 3,000 mg; |
| Gymnema at about 400 mg; |
| Ginseng; |
| L-carnitine at about 4 g; |
| Pyrroloquinoline quinone at about 20 mg; |
| Banaba leaf at about 50 mg; |
| Resveratrol at about 250 mg; |
| Pterostilbene at about 1 mg |

FIG. 9

DIABETIC TREATMENT FORMULATION (25 COMPONENTS)

| |
|---|
| bilberry extract at about 600 mg; |
| alpha lipoic acid at about 600 mg; |
| chromium picolinate at about 1200 mcg; |
| omega-3-fatty acids at about 8 g; |
| dihydroepiandrosterone at about 100 mg; |
| Blueberry extract at about 500 mg; |
| Vitamin D3 at about 5000 IU; |
| Guar gum at about 500 mg; |
| Carnosine at about 3,000 mg; |
| Cinnamomum root at about 2 g; |
| Aged garlic at about 1,000 mg; |
| Vanadium at about 50 mg; |
| Bitter melon at about 1,000 mg; |
| Green tea extract at about 450 mg; |
| Fenugreek 1:4 at about 80 mg; |
| Goat's rue; |
| Curcumin at about 8 g; |
| Glycyrrhiza glabra at about 500 mg; |
| Vitamin E at about 1,000 mg; |
| Coenzyme Q10 at about 300 mg; |
| Gymnema at about 400 mg; |
| L-carnitine at about 4 g; |
| Banaba leaf at about 50 mg; |
| Resveratrol at about 250 mg; |
| Pterostilbene at about 1 mg |

FIG. 10

EYE TREATMENT FORMULATION (20 COMPONENTS)

| |
|---|
| lutein at about 20 mg; |
| astaxanthin at about 20 mg; |
| zeaxanthin at about 10 mg; |
| Vitamin A; |
| Vitamin E at about 1,000 mg; |
| Bilberry extract at about 600 mg; |
| Blueberry extract at about 500 mg; |
| Lycopene at about 40 mg; |
| Zinc citrate at about 50 mg; |
| Quercetin at about 150 mg; |
| L-glutathione at about 250 mg; |
| N-acetyl cysteine at about 500 mg; |
| Taurine at about 400 mg; |
| Vitamin C at about 2,000 mg |
| Riboflavin B2 at about 200 mg; |
| Carnosine at about 3,000 mg; |
| Grape seed extract at about 300 mg; |
| Black currant fruit; |
| R-lipoic acid at about 600 mg; |
| Tumeric at about 400 mg |

FIG. 11

EYE TREATMENT FORMULATION (15 COMPONENTS)

| |
|---|
| lutein at about 20 mg; |
| astaxanthin at about 20 mg; |
| zeaxanthin at about 10 mg; |
| Vitamin A; |
| Vitamin E at about 1,000 mg; |
| Bilberry extract at about 600 mg; |
| Blueberry extract at about 500 mg; |
| Lycopene at about 40 mg; |
| Quercetin at about 150 mg; |
| L-glutathione at about 250 mg; |
| Taurine at about 400 mg; |
| Vitamin C at about 2,000 mg |
| Carnosine at about 3,000 mg; |
| Grape seed extract at about 300 mg; |
| Tumeric at about 400 mg |

FIG. 12

EYE TREATMENT FORMULATION (10 COMPONENTS)

| |
|---|
| lutein at about 20 mg; |
| astaxanthin at about 20 mg; |
| zeaxanthin at about 10 mg; |
| Vitamin A; |
| Bilberry extract at about 600 mg; |
| Lycopene at about 40 mg; |
| Quercetin at about 150 mg; |
| Taurine at about 400 mg; |
| Vitamin C at about 2,000 mg |
| Carnosine at about 3,000 mg; |

FIG. 13

MALE WELLNESS FORMULATION (31 COMPONENTS)

| |
|---|
| Dihydroepiandrosterone at about 100 mg; |
| Pregnenolone at about 60 mg; |
| Zinc citrate at about 60 mg; |
| Diindolylmethane at about 200 mg; |
| Chrysin at about 1500 mg; |
| Resveratrol at about 250 mg; |
| Quercetin at about 150 mg; |
| Saw palmetto at about 320 mg; |
| Finasteride at about 2.5 mg; |
| Fenugreek at about 90 mg; |
| Vitamin C at about 1,000 mg; |
| Stinging nettle at about 240 mg; |
| Norway spruce lignan extract at about 50 mg; |
| Ginger root at about 100 mg; |
| Yohimbine at about 20 mg; |
| Tribulus terrestris at about 300 mg; |
| Eurycoma longifolia at about 50 mg; |
| Muira puama at about 850 mg; |
| Maca at about 320 mg; |
| Bioperine at about 7.5 mg; |
| Pumpkin seed oil at about 200 mg; |
| Pygeum africanum at about 100 mg; |
| Lycopene at about 50 mg; |
| Mucuna pruriens at about 300 mg; |
| Red clover flower extract at about 50 mg; |
| Ginkgo biloba at about 60 mg; |
| Korean ginseng at about 50 mg; |
| Grape seed extract at about 300 mg; |
| Panax ginseng at about 100 mg; |
| Epimedium brevicornum herb; |
| Beta sitosterol at about 100 mg |

FIG. 14

MALE WELLNESS FORMULATION (25 COMPONENTS)

| |
|---|
| Dihydroepiandrosterone at about 100 mg; |
| Pregnenolone at about 60 mg; |
| Zinc citrate at about 60 mg; |
| Diindolylmethane at about 200 mg; |
| Chrysin at about 1500 mg; |
| Resveratrol at about 250 mg; |
| Quercetin at about 150 mg; |
| Saw palmetto at about 320 mg; |
| Fenugreek at about 90 mg; |
| Vitamin C at about 1,000 mg; |
| Stinging nettle at about 240 mg; |
| Norway spruce lignan extract at about 50 mg; |
| Ginger root at about 100 mg; |
| Yohimbine at about 20 mg; |
| Tribulus terrestris at about 300 mg; |
| Muira puama at about 850 mg; |
| Maca at about 320 mg; |
| Pumpkin seed oil at about 200 mg; |
| Pygeum africanum at about 100 mg; |
| Ginkgo biloba at about 60 mg; |
| Korean ginseng at about 50 mg; |
| Grape seed extract at about 300 mg; |
| Panax ginseng at about 100 mg; |
| Beta sitosterol at about 100 mg |

FIG. 15

MALE WELLNESS FORMULATION (20 COMPONENTS)

| |
|---|
| Dihydroepiandrosterone at about 100 mg; |
| Pregnenolone at about 60 mg; |
| Zinc citrate at about 60 mg; |
| Diindolylmethane at about 200 mg; |
| Chrysin at about 1500 mg; |
| Resveratrol at about 250 mg; |
| Fenugreek at about 90 mg; |
| Vitamin C at about 1,000 mg; |
| Stinging nettle at about 240 mg; |
| Norway spruce lignan extract at about 50 mg; |
| Yohimbine at about 20 mg; |
| Tribulus terrestris at about 300 mg; |
| Muira puama at about 850 mg; |
| Maca at about 320 mg; |
| Pumpkin seed oil at about 200 mg; |
| Pygeum africanum at about 100 mg; |
| Korean ginseng at about 50 mg; |
| Grape seed extract at about 300 mg; |
| Panax ginseng at about 100 mg; |
| Beta sitosterol at about 100 mg |

FIG. 16

MALE WELLNESS FORMULATION (15 COMPONENTS)

| |
|---|
| Dihydroepiandrosterone at about 100 mg; |
| Pregnenolone at about 60 mg; |
| Zinc citrate at about 60 mg; |
| Diindolylmethane at about 200 mg; |
| Chrysin at about 1500 mg; |
| Resveratrol at about 250 mg; |
| Fenugreek at about 90 mg; |
| Vitamin C at about 1,000 mg; |
| Stinging nettle at about 240 mg; |
| Norway spruce lignan extract at about 50 mg; |
| Yohimbine at about 20 mg; |
| Tribulus terrestris at about 300 mg; |
| Pygeum africanum at about 100 mg; |
| Korean ginseng at about 50 mg; |
| Beta sitosterol at about 100 mg |

FIG. 17

ANTI-OXIDANT TREATMENT FORMULATION (40 COMPONENTS)

| | |
|---|---|
| Vitamin A; | Nicotinamide adenine dinucleotide at about 50 mg; |
| Vitamin D3 at about 6,000 IU; | Methylsulfonylmethane at about 500 mg; |
| Vitamin E at about 1,000 mg; | Pregnenolone at about 60 mg; |
| Vitamin C at about 2,000 mg; | Pterostilbene at about 1 mg; |
| Vitamin K2 at about 100 mg; | Grape seed extract at about 300 mg; |
| Coenzyme Q10 at about 400 mg; | Melatonin at about 3 mg; |
| Trans-resveratrol at about 500 mg; | Ginger root extract at about 200 mg; |
| Sulphoraphane at about 225 mg; | Ginseng at about 200 mg; |
| Inositol hexanicotinate at about 1,000 mg; | Gingko biloba at about 200 mg; |
| Alpha lipoic acid at about 600 mg; | Chromium picolinate at about 1 mg |
| Bioflavonoids at about 2,000 mg; | |
| Carotenoids at about 30 mg; | |
| Alpha carotene at about 12 mg; | |
| Lutein at about 20 mg; | |
| Lycopene at about 40 mg; | |
| Aged garlic at about 1,000 mg; | |
| N-acetyl cysteine at about 600 mg; | |
| Tumeric at about 400 mg; | |
| Fisetin at about 48 mg; | |
| Quercetin at about 150 mg; | |
| Acetyl l-carnitine at about 4,000 mg; | |
| Astaxanthin at about 20 mg; | |
| Carnosine at about 3,000 mg; | |
| Dihydroepiandrosterone at about 200 mg; | |
| Bilberry extract at about 600 mg; | |
| Blueberry extract at about 500 mg; | |
| L-glutathione at about 250 mg; | |
| Zinc citrate at about 50 mg; | |
| French maritime pine bark extract at about 250 mg; | |
| Acai at about 5,000 mg; | |

FIG. 18

ANTI-OXIDANT TREATMENT FORMULATION (35 COMPONENTS)

| | |
|---|---|
| Vitamin D3 at about 6,000 IU; | Grape seed extract at about 300 mg; |
| Vitamin E at about 1,000 mg; | Melatonin at about 3 mg; |
| Vitamin C at about 2,000 mg; | Ginseng at about 200 mg; |
| Vitamin K2 at about 100 mg; | Gingko biloba at about 200 mg; |
| Coenzyme Q10 at about 400 mg; | Chromium picolinate at about 1 mg |
| Trans-resveratrol at about 500 mg; | |
| Sulphoraphane at about 225 mg; | |
| Alpha lipoic acid at about 600 mg; | |
| Bioflavonoids at about 2,000 mg; | |
| Carotenoids at about 30 mg; | |
| Alpha carotene at about 12 mg; | |
| Lutein at about 20 mg; | |
| Lycopene at about 40 mg; | |
| Aged garlic at about 1,000 mg; | |
| N-acetyl cysteine at about 600 mg; | |
| Tumeric at about 400 mg; | |
| Quercetin at about 150 mg; | |
| Acetyl l-carnitine at about 4,000 mg; | |
| Astaxanthin at about 20 mg; | |
| Carnosine at about 3,000 mg; | |
| Dihydroepiandrosterone at about 200 mg; | |
| Bilberry extract at about 600 mg; | |
| Blueberry extract at about 500 mg; | |
| L-glutathione at about 250 mg; | |
| French maritime pine bark extract at about 250 mg; | |
| Acai at about 5,000 mg; | |
| Nicotinamide adenine dinucleotide at about 50 mg; | |
| Methylsulfonylmethane at about 500 mg; | |
| Pregnenolone at about 60 mg; | |
| Pterostilbene at about 1 mg; | |

FIG. 19

ANTI-OXIDANT TREATMENT FORMULATION (30 COMPONENTS)

| |
|---|
| Vitamin D3 at about 6,000 IU; |
| Vitamin E at about 1,000 mg; |
| Vitamin C at about 2,000 mg; |
| Vitamin K2 at about 100 mg; |
| Coenzyme Q10 at about 400 mg; |
| Trans-resveratrol at about 500 mg; |
| Sulphoraphane at about 225 mg; |
| Alpha lipoic acid at about 600 mg; |
| Bioflavonoids at about 2,000 mg; |
| Carotenoids at about 30 mg; |
| Alpha carotene at about 12 mg; |
| Lutein at about 20 mg; |
| Lycopene at about 40 mg; |
| Aged garlic at about 1,000 mg; |
| Tumeric at about 400 mg; |
| Quercetin at about 150 mg; |
| Acetyl l-carnitine at about 4,000 mg; |
| Astaxanthin at about 20 mg; |
| Carnosine at about 3,000 mg; |
| Dihydroepiandrosterone at about 200 mg; |
| Bilberry extract at about 600 mg; |
| Blueberry extract at about 500 mg; |
| L-glutathione at about 250 mg; |
| Methylsulfonylmethane at about 500 mg; |
| Pregnenolone at about 60 mg; |
| Pterostilbene at about 1 mg; |
| Grape seed extract at about 300 mg; |
| Melatonin at about 3 mg; |
| Ginseng at about 200 mg; |
| Gingko biloba at about 200 mg; |

FIG. 20

ANTI-OXIDANT TREATMENT FORMULATION (25 COMPONENTS)

| |
|---|
| Vitamin D3 at about 6,000 IU; |
| Vitamin E at about 1,000 mg; |
| Vitamin C at about 2,000 mg; |
| Vitamin K2 at about 100 mg; |
| Coenzyme Q10 at about 400 mg; |
| Trans-resveratrol at about 500 mg; |
| Sulphoraphane at about 225 mg; |
| Alpha lipoic acid at about 600 mg; |
| Lutein at about 20 mg; |
| Lycopene at about 40 mg; |
| Aged garlic at about 1,000 mg; |
| Tumeric at about 400 mg; |
| Quercetin at about 150 mg; |
| Astaxanthin at about 20 mg; |
| Carnosine at about 3,000 mg; |
| Dihydroepiandrosterone at about 200 mg; |
| Bilberry extract at about 600 mg; |
| Blueberry extract at about 500 mg; |
| L-glutathione at about 250 mg; |
| Methylsulfonylmethane at about 500 mg; |
| Pregnenolone at about 60 mg; |
| Pterostilbene at about 1 mg; |
| Grape seed extract at about 300 mg; |
| Melatonin at about 3 mg; |
| Gingko biloba at about 200 mg; |

FIG. 21

ANTI-AGING SKIN FORMULATION (14 COMPONENTS)

| |
|---|
| Hyaluronic acid at about 0.5%; |
| Coenzyme Q10 at about 1%; |
| Estriol at about 0.4%; |
| Retinoic Acid at about 0.025%; |
| Alpha lipoic acid at about 5%; |
| Vitamin C ester at about 5%; |
| Dimethylethanolamine at about 3%; |
| Peptides; |
| Green tea extract; |
| Squalane; |
| Vitamin B3 at about 5%; |
| Teprenone; |
| Caprylic acid; |
| Acetyl hexapeptide at about 5% |

FIG. 22

ANTI-AGING SKIN FORMULATION (12 COMPONENTS)

| |
|---|
| Hyaluronic acid at about 0.5%; |
| Coenzyme Q10 at about 1%; |
| Estriol at about 0.4%; |
| Retinoic Acid at about 0.025%; |
| Alpha lipoic acid at about 5%; |
| Vitamin C ester at about 5%; |
| Dimethylethanolamine at about 3%; |
| Green tea extract; |
| Squalane; |
| Vitamin B3 at about 5%; |
| Caprylic acid; |
| Acetyl hexapeptide at about 5% |

FIG. 23

ANTI-AGING SKIN FORMULATION (10 COMPONENTS)

| |
|---|
| Hyaluronic acid at about 0.5%; |
| Coenzyme Q10 at about 1%; |
| Estriol at about 0.4%; |
| Retinoic Acid at about 0.025%; |
| Alpha lipoic acid at about 5%; |
| Vitamin C ester at about 5%; |
| Dimethylethanolamine at about 3%; |
| Squalane; |
| Vitamin B3 at about 5%; |
| Caprylic acid; |

FIG. 24

MULTIVITAMIN-MINERAL REGIMENS FOR LONGEVITY AND WELLNESS

CROSS REFERENCE

This application claims priority to U.S. patent application Ser. No. 13/043,056 filed Mar. 8, 2011 and U.S. patent application Ser. No. 13/043,216 filed Mar. 8, 2011, the specifications of which are incorporated herein by reference in their entirety.

BACKGROUND OF THE INVENTION

The present invention features novel dietary supplements, which may benefit individuals suffering from various conditions such as nutritional deficiencies, vitamin deficiencies, aging, cancer, dementia/Alzheimer's disease, high blood pressure, high cholesterol, coronary artery disease, stroke, and mental cognition.

The content of this patent application is presented solely for the purpose of being reviewed by the United States Patent and Trademark Office for patentability of the claimed novel dietary supplement. In accordance with the Dietary Supplement Health and Education Act of 1994 (DSHEA), Applicant asserts that statements made within this patent application have not been evaluated by the Food and Drug Administration. Further in accordance with DSHEA, Applicant asserts that the novel dietary supplement is not intended to diagnose, treat, prevent, mitigate or cure disease.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

The present invention features novel dietary supplements or formulations. For example, the present invention features longevity formulations, anti-dementia formulations, diabetic treatment formulations, eye treatment formulations, male wellness formulations, anti-oxidant formulations, and anti-aging skin formulations.

The present invention features a diabetic treatment formulation. In some embodiments, the diabetic treatment formulation is effective for reducing blood sugar levels. In some embodiments, the diabetic treatment formulation comprises at least 25 of the following supplemental components: bilberry extract at about 600 mg; alpha lipoic acid at about 600 mg; chromium picolinate at about 1200 mg; omega-3-fatty acids at about 8 g; dihydroepiandrosterone at about 100 mg; Blueberry extract at about 500 mg; Biotin at about 8 mg; Vitamin D3 at about 5000 IU; Taurine at about 3000 mg; Psyllium at about 5 g; Guar gum at about 500 mg; Carnosine at about 3,000 mg; *Cinnamomum* root at about 2 g; Aged garlic at about 1,000 mg; Vanadium at about 50 mg; Bitter melon at about 1,000 mg; Green tea extract at about 450 mg; Zinc citrate at about 50 mg; Fenugreek 1:4 at about 80 mg; Vitamin B6 at about 200 mg; Goat's rue; Curcumin at about 8 g; *Glycyrrhiza glabra* at about 500 mg; Vitamin E at about 1,000 mg; Coenzyme Q10 at about 300 mg; Vitamin C at about 3,000 mg; Manganese at about 10 mg; Gymnema at about 400 mg; L-argenine at about 10 g; *Ginseng*; L-carnitine at about 4 g; Pyrroloquinoline quinone at about 20 mg; Amla extract; Brown seaweed extract; Bladderwrack; Banaba leaf at about 50 mg; Bromocriptine at about 2.5 mg; Benfotiamine at about 400 mg; Resveratrol at about 250 mg; Pterostilbene at about 1 mg.

In some embodiments, the diabetic treatment formulation comprises at least 20 of the above components, e.g., 20 components, 21 components, 22 components, 23 components, 24 components. In some embodiments, the diabetic treatment formulation comprises at least 25 of the above components, e.g., 25 components, 26 components, 27 components, 28 components, 29 components. In some embodiments, the diabetic treatment formulation comprises at least 30 of the above components, e.g., 30 components, 31 components, 32 components, 33 components, 34 components. In some embodiments, the diabetic treatment formulation comprises at least 35 of the above components, e.g., 35 components, 36 components, 37 components, 38 components, 39 components, 40 components.

In some embodiments, the diabetic treatment formulation comprises bilberry extract at about 600 mg; alpha lipoic acid at about 600 mg; chromium picolinate at about 1200 mg; omega-3-fatty acids at about 8 g; dihydroepiandrosterone at about 100 mg; Blueberry extract at about 500 mg; Vitamin D3 at about 5000 IU; Guar gum at about 500 mg; Carnosine at about 3,000 mg; *Cinnamomum* root at about 2 g; Aged garlic at about 1,000 mg; Vanadium at about 50 mg; Bitter melon at about 1,000 mg; Green tea extract at about 450 mg; Fenugreek 1:4 at about 80 mg; Goat's rue; Curcumin at about 8 g; *Glycyrrhiza glabra* at about 500 mg; Vitamin E at about 1,000 mg; Coenzyme Q10 at about 300 mg; Gymnema at about 400 mg; L-carnitine at about 4 g; Banaba leaf at about 50 mg; Resveratrol at about 250 mg; Pterostilbene at about 1 mg. In some embodiments, the diabetic treatment formulation further comprises Psyllium at about 5 g. In some embodiments, the diabetic treatment formulation further comprises Zinc citrate at about 50 mg. In some embodiments, the diabetic treatment formulation further comprises Vitamin C at about 3,000 mg. In some embodiments, the diabetic treatment formulation further comprises *Ginseng*. In some embodiments, the diabetic treatment formulation further comprises Pyrroloquinoline quinone at about 20 mg. In some embodiments, the diabetic treatment formulation further comprises two of: Psyllium at about 5 g, Zinc citrate at about 50 mg, Vitamin C at about 3,000 mg, *Ginseng*, Pyrroloquinoline quinone at about 20 mg. In some embodiments, the diabetic treatment formulation further comprises three of: Psyllium at about 5 g, Zinc citrate at about 50 mg, Vitamin C at about 3,000 mg, *Ginseng*, Pyrroloquinoline quinone at about 20 mg. In some embodiments, the diabetic treatment formulation further comprises four of: Psyllium at about 5 g, Zinc citrate at about 50 mg, Vitamin C at about 3,000 mg, *Ginseng*, Pyrroloquinoline quinone at about 20 mg.

In some embodiments, the diabetic treatment formulation comprises bilberry extract at about 600 mg; alpha lipoic acid at about 600 mg; chromium picolinate at about 1200 mg; omega-3-fatty acids at about 8 g; dihydroepiandrosterone at about 100 mg; Blueberry extract at about 500 mg; Vitamin D3 at about 5000 IU; Psyllium at about 5 g; Guar gum at about 500 mg; Carnosine at about 3,000 mg; *Cinnamomum* root at about 2 g; Aged garlic at about 1,000 mg; Vanadium at about 50 mg; Bitter melon at about 1,000 mg; Green tea extract at about 450 mg; Zinc citrate at about 50 mg; Fenugreek 1:4 at about 80 mg; Goat's rue; Curcumin at about 8 g; *Glycyrrhiza glabra* at about 500 mg; Vitamin E at about 1,000 mg; Coenzyme Q10 at about 300 mg: Vitamin C at about 3,000 mg; Gymnema at about 400 mg; *Ginseng*; L-carnitine at about 4 g;

Pyrroloquinoline quinone at about 20 mg; Banaba leaf at about 50 mg; Resveratrol at about 250 mg; Pterostilbene at about 1 mg.

In some embodiments, the diabetic treatment formulation further comprises L-argenine at about 10 g. In some embodiments, the diabetic treatment formulation further comprises Brown seaweed extract. In some embodiments, the diabetic treatment formulation further comprises Bladderwrack. In some embodiments, the diabetic treatment formulation further comprises Bromocriptine at about 2.5 mg. In some embodiments, the diabetic treatment formulation further comprises Benfotiamine at about 400 mg. In some embodiments, the diabetic treatment formulation further comprises two of: L-argenine at about 10 g, Brown seaweed extract, Bladderwrack, Bromocriptine at about 2.5 mg, Benfotiamine at about 400 mg. In some embodiments, the diabetic treatment formulation further comprises three of: L-argenine at about 10 g, Brown seaweed extract, Bladderwrack, Bromocriptine at about 2.5 mg, Benfotiamine at about 400 mg.

BRIEF DESCRIPTION OF THE DRAWINGS

FIG. 1 shows an example of the longevity formulation comprising 50 ingredients.

FIG. 2 shows an example of the longevity formulation comprising 40 ingredients.

FIG. 3 shows an example of the longevity formulation comprising 35 ingredients.

FIG. 4 shows an example of the longevity formulation comprising 30 ingredients.

FIG. 5 shows an example of the anti-dementia formulation comprising 40 ingredients.

FIG. 6 shows an example of the anti-dementia formulation comprising 30 ingredients.

FIG. 7 shows an example of the anti-dementia formulation comprising 25 ingredients.

FIG. 8 shows an example of the diabetic treatment formulation comprising 35 ingredients.

FIG. 9 shows an example of the diabetic treatment formulation comprising 30 ingredients.

FIG. 10 shows an example of the diabetic treatment formulation comprising 25 ingredients.

FIG. 11 shows an example of the eye treatment formulation comprising 20 ingredients.

FIG. 12 shows an example of the eye treatment formulation comprising 15 ingredients.

FIG. 13 shows an example of the eye treatment formulation comprising 10 ingredients.

FIG. 14 shows an example of the male wellness formulation comprising 30 ingredients.

FIG. 15 shows an example of the male wellness formulation comprising 25 ingredients.

FIG. 16 shows an example of the male wellness formulation comprising 20 ingredients.

FIG. 17 shows an example of the male wellness formulation comprising 15 ingredients.

FIG. 18 shows an example of the anti-oxidant formulation comprising 40 ingredients.

FIG. 19 shows an example of the anti-oxidant formulation comprising 35 ingredients.

FIG. 20 shows an example of the anti-oxidant formulation comprising 30 ingredients.

FIG. 21 shows an example of the anti-oxidant formulation comprising 25 ingredients.

FIG. 22 shows an example of the anti-aging skin formulation comprising 14 ingredients.

FIG. 23 shows an example of the anti-aging skin formulation comprising 12 ingredients.

FIG. 24 shows an example of the anti-aging skin formulation comprising 10 ingredients.

DESCRIPTION OF PREFERRED EMBODIMENTS

The present invention features novel dietary supplements (multivitamin-mineral formulations), hereinafter referred to "formulation" or "formulations."

Longevity Formulations

The present invention features longevity formulations. In some embodiments, the formulation comprises at least 30 of the following supplemental components: Pregnenolone at about 30 mg; natto kinase at about 300 mg; vitamin K2 at about 32 mg; coenzyme Q10 at about 300 mg; acetyl L-carnitine arginate at about 700 mg; L-glutathione at about 250 mg; vitamin A (e.g., as beta-carotene at about 25000 IU; palmitate at about 2500 IU); vitamin C at about 2000 mg (e.g., as ascorbic acid and ascorbyl palmitate); vitamin D3 (e.g., as cholecalciferol) at about 8000 IU; vitamin E (e.g., as mixed tocotrienols gamma/delta) at about 1000 mg; thiamine B1 at about 50 mg; riboflavin B2 at about 200 mg; niacinamide at about 1000 mg; vitamin B6 (e.g., as pyridoxine hydrochloride/pyridoxol 5-phosphate coenymated) at about 200 mg; folate (e.g., as folic acid and calcium folinate) at about 1 mg; vitamin B12 (e.g., as methyl cobalamin) at about 2000 mg; biotin at about 6 mg; pantothenic acid (e.g., as calcium d-panthothenate and panthethine) at about 500 mg; calcium (e.g., as calcium carbonate, malate, amino acid cholate or citrate) at about 1000 mg; iodine (e.g., as potassium iodine) at about 220 mg; magnesium (e.g.; as magnesium amino acid chelate) at about 1000 mg; zinc (e.g., as monomethionine plus zinc citrate) at about 40 mg; selenium (e.g., as l-selenomethionine plus sodium selenite) at about 200 mg; copper (e.g., as copper sebacate) at about 2.5 mg; manganese (e.g., as manganese citrate) at about 5 mg; chromium (e.g., as chromium polynicotinate/histidinate) at about 1200 mg; molybdenum (e.g., as molybdenum amino acid chelate) at about 2000 mg; sodium at about 5 mg; potassium at about 50 mg; aged garlic at about 1000 mg; N-acetyl cysteine at about 600 mg; vacadyl sulphate at about 400 mg; silymarin (milk thistle extract) at about 600 mg; D-ribose at about 10 grams; indole 3 carbinol at about 200 mg; sulphoramane 225 mg at about 225 mg; cranberry (vaccinium macrocarpon) at about 1000 mg; French maritime pine bark extract (e.g., PYCNOGENOL®) at about 250 mg; l-glutathione at about 250 mg; *cinnamomum* root at about 4000 mg; choline (e.g., as bitartrate) at about 1000 mg; inositol at about 1000 mg; alpha-lipoic acid and/or r lipoic acid at about 600 mg; polygonum cuspidatum root extract at about 1000 mg (e.g., standardized to 53% trans-reservatrol); dimethylaminoethanol (e.g., as bitartrate) at about 30 mg; grape seed extract at about 300 mg; methylsulfonylmethane at about 250 mg; hawthorn berry extract at about 1500 mg; N-acetyl tyrosine at about 25 mg; turmeric extract (e.g., rhizome) (e.g., 95% curcumin) at about 8 gms; green tea extract (e.g., 95% pomphenols, solution epogalocatequina galato); gingko leaf extract (50:1) (e.g., 25% flavonglylosides) at about 140 mg; bilberry extracts (e.g., 25% anthocyanins) at about 600 mg; rutin at about 100 mg; blain pepper fruit extract (bioperine) at about 3 mg; lycopene at about 110 mg; boron (e.g., as amino acid chelate) at about 12 mg; lutein at about 20 mg; astaxanthin at about 20 mg; bitter melon at about 1000 mg; dehydroepiandrosterone at about 2000 mg; black currant seed at about 2000 mg; carnosine at about 3 gms; conjugated linoleic acid at about 3000 mg; and hyaluronic acid at about 80 mg.

In some embodiments, the formulation comprises at least 35 of the above components. In some embodiments, the formulation comprises at least 40 of the above components. In some embodiments, the formulation comprises at least 45 of the above components. In some embodiments, the formulation comprises at least 50 of the above components. In some embodiments, the formulation comprises at least 55 of the above components. In some embodiments, the formulation comprises at least 60 of the above components. FIG. 1-4 show examples of longevity formulations comprising 50 of the above components, 40 of the above components, 35 of the above components, and 30 of the above components, respectively.

Anti-Dementia Formulations

The present invention also features anti-dementia formulations. In some embodiments, the formulation comprises at least 25 of the following supplemental components: idebenone at about 180 mg; rhodiola at about 400 mg; gingko biloba at about 160 mg; thionine at about 400 mg; huperzine a at about 2 mg; coenzyme Q10 at about 400 mg; alpha lipoic acid at about 600 mg; melatonin at about 3 mg; omega 3 fatty acid at about 6000 mg; zinc carnosine at about 500 mg; magnesium at about 1000 mg; vitamin E (e.g., mixed tocotrienols gamma/delta) at about 1000 mg; N-acetyl cysteine at about 1200 mg; dehydroepiandrosterone (DHEA) at about 100 mg; pregnenolone at about 60 mg; niacin at about 1000 mg; phosphatidylserine docasahexanenoic acid at about 300 mg; vitamin B12 at about 2000 mg; vitamin B6 at about 200 mg; iron at about 18 mg; vinpocetine at about 40 mg; phospholipid grape seed extract at about 300 mg; blueberry extract at about 300 mg; acetyl carnitine arginate 900 mg; ashwagandha extract (e.g., SENSORIL®) at about 250 mg; uridine 5 monophosphate at about 100 mg; French maritime pine bark extract (e.g., PYCNOGENOL®) at about 250 mg; L-alpha-glycerylphosphorylcholine at about 1500 mg; curcumin at about 8 gms; coconut oil at about 1000 mg; astaxanthin at about 20 mg; chromium picolinate at about 1200 mg; carnosine at about 3000 mg; n-acetyl-tyrosine at about 1500 mg; phenylalanine at about 1500 mg; quercetin at about 150 mg; inositol hexanicotinate at about 1000 mg; dimethylethanolamine (DMAE) at about 100 mg; s-adenosylmethionine at about 400 mg; riboflavin 32 at about 200 mg; thiamine B1 at about 50 mg; selenium (e.g., as L-selenomethionine sodium selenite) at about 200 mg; colostrum at about 4000 mg; lecithin (e.g., 26% phosphaticylcholine) at about 300 mg; and vitamin D2 at about 8000 IU.

In some embodiments, the formulation comprises at least 30 of the above components. In some embodiments, the formulation comprises at least 35 of the above components. In some embodiments, the formulation comprises at least 40 of the above components. FIG. 5-7 show examples of anti-dementia formulations comprising 40 of the above components, 30 of the above components, and 25 of the above components, respectively.

Diabetic Treatment Formulations

The present invention also features diabetic treatment formulations. In some embodiments, the formulation comprises at least 25 of the following supplemental components: bilberry extract at about 600 mg; alpha lipoic acid at about 600 mg; chromium picolinate at about 1200 mg; omega-3-fatty acids at about 8 g; dihydroepiandrosterone (DHEA) at about 100 mg; Blueberry extract at about 500 mg; Biotin at about 8 mg; Vitamin D3 at about 5000 IU; Taurine at about 3000 mg; Psyllium at about 5 g; Guar gum at about 500 mg; Carnosine at about 3,000 mg; *Cinnamomum* root at about 2 g; Aged garlic at about 1,000 mg; Vanadium at about 50 mg; Bitter melon at about 1,000 mg; Green tea extract at about 450 mg; Zinc citrate at about 50 mg; Fenugreek (1:4) extract (e.g., *trigonella foenum-graecum*) at about 80 mg; Vitamin B6 at about 200 mg; Goat's rue (e.g., *galega officinalis*); Curcumin at about 8 g; *Glycyrrhiza glabra* at about 500 mg; Vitamin E at about 1,000 mg; Coenzyme Q10 at about 300 mg; Vitamin C at about 3,000 mg; Manganese at about 10 mg; Gymnema at about 400 mg; L-argenine at about 10 g; *Ginseng*; L-carnitine at about 4 g; Pyrroloquinoline quinone (PQQ) at about 20 mg; Amla extract (Indian gooseberry); Brown seaweed extract; Bladderwrack; Banaba leaf at about 50 mg; Bromocriptine at about 2.5 mg; Benfotiamine at about 400 µg; Resveratrol at about 250 mg; and Pterostilbene at about 1 mg.

In some embodiments, the formulation comprises at least 30 of the above components. In some embodiments, the formulation comprises at least 35 of the above components. FIG. 8-10 show examples of diabetic treatment formulations comprising 35 of the above components, 30 of the above components, and 25 of the above components, respectively.

In some embodiments, the formulation further comprises testosterone cypionate at about 100 mg (administered IM). In some embodiments, the formulation further comprises female testosterone at about 30 mg (administered IM). In some embodiments, the psyllium is administered 3 times per day. In some embodiments, the guar gum is administered 3 times per day.

Eye Treatment Formulations

The present invention also features eye treatment formulations (e.g., macular degeneration formulations, cataract formulations, etc.). In some embodiments, the formulation comprises at least 10 of the following supplemental components: lutein at about 20 mg; astaxanthin at about 20 mg; Vitamin A (e.g., as beta carotene 20,000 IU, palmitate 2,500 IU); Vitamin E at about 1,000 mg; (e.g., gamma/delta mixed tocotrienols); Rutin at about 100 mg; Selenium at about 200 mg (e.g., L-selenomethionine plus sodium selenite); Bilberry extract at about 600 mg; Blueberry extract at about 500 mg; French maritime pine bark extract at about 250 mg; Lycopene at about 40 mg; Zinc citrate at about 50 mg; Quercetin at about 150 mg; Chromium picolinate at about 1200 mg; L-glutathione at about 250 mg; N-acetyl cysteine at about 500 mg; Taurine at about 400 mg; Vitamin C at about 2,000 mg (e.g., as ascorbic acid, ascorbyl palmitate); Riboflavin B2 at about 200 mg; Hyaluronic acid at about 80 mg; Carnosine at about 3,000 mg; Grape seed extract at about 300 mg; Black currant fruit; R-lipoic acid at about 600 mg; Tumeric at about 400 mg; and Vitamin B6 at about 200 mg.

In some embodiments, the formulation comprises at least 15 of the above components. In some embodiments, the formulation comprises at least 20 of the above components. FIG. 11-13 show examples of eye treatment formulations comprising 20 of the above components, 15 of the above components, and 10 of the above components, respectively.

Male Wellness Formulations

The present invention also features male wellness formulations, e.g., male treatment formulations (e.g., to increase testosterone). In some embodiments, the formulation comprises at least 15 of the following supplemental components:

Dihydroepiandrosterone at about 100 mg; Pregnenolone at about 60 mg; Zinc citrate at about 60 mg; Diindolylmethane at about 200 mg; Chrysin at about 1500 mg; Resveratrol at about 250 mg; Quercetin at about 150 mg; Saw palmetto at about 320 mg; Finasteride at about 2.5 mg; Fenugreek at about 90 mg; Vitamin C at about 1,000 mg; Stinging nettle at about 240 mg; Boron at about 3 mg; Norway spruce lignan extract at about 50 mg; Ginger root at about 100 mg; Yohimbine at about 20 mg; *Tribulus terrestris* at about 300 mg; *Eurycoma longifolia* at about 50 mg; *Muira puama* at about 850 mg; Maca at about 320 mg; Bioperine at about 7.5 mg; Cernilton (e.g., Cernitin®) at about 250 mg; Pumpkin seed oil at about 200 mg; *Pygeum africanum* at about 100 mg; Lycopene at about 50 mg; *Mucuna pruriens* at about 300 mg; Red clover flower extract at about 50 mg; *Ginkgo biloba* at about 60 mg; Korean *ginseng* at about 50 mg; Grape seed extract at about 300 mg; *Panax ginseng* at about 100 mg; Ashwagandha at about 300 mg; *Epimedium brevicornum* herb; Selenium at about 100 mg; Beta sitosterol at about 100 mg.

In some embodiments, the formulation comprises at least 20 of the above components. In some embodiments, the formulation comprises at least 25 of the above components. In some embodiments, the formulation comprises at least 30 of the above components. FIG. 14-17 show examples of male wellness formulations comprising 30 of the above components, 25 of the above components, 20 of the above components, and 15 of the above components, respectively.

Anti-Oxidant Formulations

The present invention also features anti-oxidant formulations. In some embodiments, the formulation comprises at least 25 of the following supplemental components: Vitamin A (e.g., as betacarotene 20,000 IU, palmitate 2500 IU); Vitamin D3 at about 6,000 IU; Vitamin E at about 1,000 mg (e.g., mixed tocotrienols gamma/delta); Vitamin C at about 2,000 mg (e.g., as ascorbic acid and ascorbyl palmitate); Vitamin K2 at about 100 mg; Coenzyme Q10 at about 400 mg; Trans-resveratrol at about 500 mg; Sulphoraphane at about 225 mg; Inositol hexanicotinate at about 1,000 mg; Alpha lipoic acid at about 600 mg; Bioflavonoids at about 2,000 mg; Carotenoids at about 30 mg; Alpha carotene at about 12 mg; Lutein at about 20 mg; Lycopene at about 40 mg; Aged garlic at about 1,000 mg; N-acetyl cysteine at about 600 mg; Tumeric at about 400 mg; Fisetin at about 48 mg; Quercetin at about 150 mg; Acetyl 1-carnitine at about 4,000 mg; Astaxanthin at about 20 mg; Idebenone at about 180 mg; Carnosine at about 3,000 mg; Dihydroepiandrosterone at about 200 mg; Bilberry extract at about 600 mg; Blueberry extract at about 500 mg; L-glutathione at about 250 mg; Zinc citrate at about 50 mg; Selenium at about 200 mg (e.g., as L-selenomethionine+sodium selenite); French maritime pine bark extract at about 250 mg; Acai at about 5,000 mg; Nicotinamide adenine dinucleotide at about 50 mg; Methylsulfonylmethane (MSM) at about 500 mg; Pregnenolone at about 60 mg; Hyaluronic acid at about 80 mg; Hawthorne extract at about 1,200 mg; L-argenine at about 10 g; L-Taurine at about 4 g; Pterostilbene at about 1 mg; Grape seed extract at about 300 mg; Melatonin at about 3 mg; Ginger root extract at about 200 mg; Rutin at about 5 mg; *Ginseng* at about 200 mg; *Gingko biloba* at about 200 mg; and Chromium picolinate at about 1 mg.

In some embodiments, the formulation comprises at least 30 of the above components. In some embodiments, the formulation comprises at least 35 of the above components. In some embodiments, the formulation comprises at least 40 of the above components. FIG. 18-21 show examples of anti-oxidant formulations comprising 40 of the above components, 35 of the above components, 30 of the above components, and 25 of the above components, respectively.

Anti-Aging Skin Formulations

The present invention also features anti-aging skin formulations (e.g., skin creams). In some embodiments, the formulation comprises at least 10 of the following supplemental components Idebenone at about 1%; Hyaluronic acid at about 0.5%; Coenzyme Q10 at about 1%; Estriol at about 0.4%; Retinoic Acid at about 0.025%; Alpha lipoic acid at about 5%; Vitamin C ester at about 5%; Dimethylethanolarnine (DMAE) at about 3%; Peptides (peptides for skin creams are well known to one of ordinary skill in the art, e.g., peptides derived from collagen, peptides derived from elastin, palmitoyl pentapeptide, etc.); Green tea extract; Squalane; Vitamin B3 at about 5%; Teprenone (e.g., geranyl geranylacetone); Caprylic acid (e.g., palm/coconut oils); and Acetyl hexapeptide at about 5%.

In some embodiments, the formulation comprises at least 12 of the above components. In some embodiments, the formulation comprises at least 14 of the above components. FIG. 22-24 show examples of anti-aging skin formulations comprising 14 of the above components, 12 of the above components, and 10 of the above components, respectively.

In some embodiments, a formulation of the present invention is administered to a human patient once a day. In some embodiments, a formulation of the present invention is administered to a human patient once a week.

The formulations of the present invention may be a solid tablet, granule, syrup or liquid form. One of ordinary skill would be able to prepare an appropriate form of any formulation of the present invention.

As used herein, the unit "mg", for example iodine (as potassium iodine) at about 220 mg, means micrograms.

A ratio recited above, for example a ratio of 50:1 recited above, for example gingko leaf extract (50:1), means 50 parts of the extract to 1 part of water.

As used herein, the term "about" refers to plus or minus 10% of the referenced number. For example, an embodiment comprising uridine 5 monophosphate at about 100 mg includes uridine 5 monophosphate between 90 and 110 mg.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A formulation comprising at least 25 of the following supplemental components:
   (i) bilberry extract at about 600 mg:
   (ii) alpha lipoic add at about 600 mg;
   (iii) chromium picolinate at about 1200 mcg;
   (iv) omega-3-fatty acids at about 8 g;
   (v) dehydroepiandrosterone at about 100 mg;
   (vi) Blueberry extract at about 500 mg;
   (vii) Biotin at about 8 mg;
   (viii) Vitamin D3 at about 5000 IU;
   (ix) Taurine at about 3000 mg;
   (x) Psyllium at about 5 g;
   (xi) Guar gum at about 500 mg;
   (xii) Carnosine at about 3,000 mg;
   (xiii) *Cinnamomum* root at about 2 g;
   (xiv) Aged garlic at about 1,000 mg;
   (xv) Vanadium at about 50 mg;
   (xvi) Bitter melon at about 1,000 mg;
   (xvii) Green tea extract at about 450 mg;
   (xviii) Zinc citrate at about 50 mg;
   (xix) Fenugreek 1:4 at about 80 mg;
   (xx) Vitamin B6 at about 200 mg;
   (xxi) Goat's rue;
   (xxii) Curcumin at about 8 g;

(xxiii) *Glycyrrhiza glabra* at about 500 mg;
(xxiv) Vitamin E at about 1,000 mg;
(xxv) Coenzyme Q10 at about 300 mg;
(xxvi) Vitamin C at about 3,000 mg;
(xxvii) Manganese at about 10 mg;
(xxviii) Gymnema at about 400 mg;
(xxix) L-argenine at about 10 g;
(xxx) *Ginseng*;
(xxxi) L-carnitine at about 4 g;
(xxxii) Pyrroloquinoline quinone at about 20 mg;
(xxxiii) Amla extract;
(xxxiv) Brown seaweed extract;
(xxxv) Bladderwrack;
(xxxvi) Banaba leaf at about 50 mg;
(xxxvii) Bromocriptine at about 2.5 mg;
(xxxviii) Benfotiamine at about 400 mg;
(xxxix) Resveratrol at about 250 mg; and
(xl) Pterostilbene at about 1 mg,
wherein the formulation is effective for reducing a blood sugar level.

2. The formulation of claim 1 comprising at least 30 of components (i) through (xl).

3. The formulation of claim 1 comprising at least 35 of components (i) through (xl).

4. A formulation comprising:
(i) bilberry extract at about 600 mg;
(ii) alpha lipoic acid at about 600 mg;
(iii) chromium picolinate at about 1200 mg;
(iv) omega-3-fatty acids at about 8 g;
(v) dehydroepiandrosterone at about 100 mg;
(vi) Blueberry extract at about 500 mg;
(vii) Vitamin D3 at about 5000 IU;
(viii) Guar gum at about 500 mg;
(ix) Carnosine at about 3,000 mg;
(x) *Cinnamomum* root at about 2 g;
(xi) Aged garlic at about 1,000 mg;
(xii) Vanadium at about 50 mg;
(xiii) Bitter melon at about 1,000 mg;
(xiv) Green tea extract at about 450 mg;
(xv) Fenugreek 1:4 at about 80 mg;
(xvi) Goat's rue;
(xvii) Curcumin at about 8 g;
(xviii) *Glycyrrhiza glabra* at about 500 mg;
(xix) Vitamin E at about 1,000 mg;
(xx) Coenzyme Q10 at about 300 mg;
(xxi) Gymnema at about 400 mg;
(xxii) L-carnitine at about 4 g;
(xxiii) Banaba leaf at about 50 mg;
(xxiv) Resveratrol at about 250 mg; and
(xxv) Pterostilbene at about 1 mg;
wherein the formulation is effective for reducing a blood sugar level.

5. The formulation of claim 4 further comprising Psyllium at about 5 g.

6. The formulation of claim 4 further comprising Zinc citrate at about 50 mg.

7. The formulation of claim 4 further comprising Vitamin C at about 3,000 mg.

8. The formulation of claim 4 further comprising *Ginseng*.

9. The formulation of claim 4 further comprising Pyrroloquinoline quinone at about 20 mg.

10. The formulation of claim 4 further comprising two of: Psyllium at about 5 g, Zinc citrate at about 50 mg, Vitamin C at about 3,000 mg, *Ginseng*, Pyrroloquinoline quinone at about 20 mg.

11. The formulation of claim 4 further comprising three of: Psyllium at about 5 g, Zinc citrate at about 50 mg, Vitamin C at about 3,000 mg, *Ginseng*, Pyrroloquinoline quinone at about 20 mg.

12. The formulation of claim 4 further comprising four of: Psyllium at about 5 g, Zinc citrate at about 50 mg, Vitamin C at about 3,000 mg, *Ginseng*, Pyrroloquinoline quinone at about 20 mg.

13. A formulation comprising:
(i) bilberry extract at about 600 mg;
(ii) alpha lipoic acid at about 600 mg;
(iii) chromium picolinate at about 1200 mg;
(iv) omega-3-fatty acids at about 8 g;
(v) dehydroepiandrosterone at about 100 mg;
(vi) Blueberry extract at about 500 mg;
(vii) Vitamin D3 at about 5000 IU;
(viii) Psyllium at about 5 g;
(ix) Guar gum at about 500 mg;
(x) Carnosine at about 3,000 mg;
(xi) *Cinnamomum* root at about 2 g;
(xii) Aged garlic at about 1,000 mg;
(xiii) Vanadium at about 50 mg;
(xiv) Bitter melon at about 1,000 mg;
(xv) Green tea extract at about 450 mg;
(xvi) Zinc citrate at about 50 mg;
(xvii) Fenugreek 1:4 at about 80 mg;
(xviii) Goat's rue;
(xix) Curcumin at about 8 g;
(xx) *Glycyrrhiza glabra* at about 500 mg;
(xxi) Vitamin E at about 1,000 mg;
(xxii) Coenzyme Q10 at about 300 mg;
(xxiii) Vitamin C at about 3,000 mg;
(xxiv) Gymnema at about 400 mg;
(xxv) *Ginseng*;
(xxvi) L-carnitine at about 4 g;
(xxvii) Pyrroloquinoline quinone at about 20 mg;
(xxviii) Banaba leaf at about 50 mg;
(xxix) Resveratrol at about 250 mg; and
(xxx) Pterostilbene at about 1 mg;
wherein the formulation is effective for reducing a blood sugar level.

14. The formulation of claim 13 further comprising L-argenine at about 10 g.

15. The formulation of claim 13 further comprising Brown seaweed extract.

16. The formulation of claim 13 further comprising Bladderwrack.

17. The formulation of claim 13 further comprising Bromocriptine at about 2.5 mg.

18. The formulation of claim 13 further comprising Benfotiamine at about 400 mg.

19. The formulation of claim 13 further comprising two of: L-argenine at about 10 g, Brown seaweed extract, Bladderwrack, Bromocriptine at about 2.5 mg, Benfotiamine at about 400 mg.

20. The formulation of claim 13 further comprising three of: L-argenine at about 10 g, Brown seaweed extract, Bladderwrack, Bromocriptine at about 2.5 mg, Benfotiamine at about 400 mg.

* * * * *